(12) United States Patent
Del Rio et al.

(10) Patent No.: US 9,914,948 B2
(45) Date of Patent: Mar. 13, 2018

(54) POST-TREATMENT TO ENHANCE THE ENZYMATIC HYDROLYSIS OF PRETREATED LIGNOCELLULOSIC BIOMASS

(71) Applicant: FPInnovations, Ponite-Claire (CA)

(72) Inventors: Luis Fernando Del Rio, Pointe-Claire (CA); Waleed Wafa Al Dajani, Pierrefonds (CA); Changbin Mao, Pierrefonds (CA); Zhirun Yuan, Pointe-Claire (CA)

(73) Assignee: FPInnovations, St-Jean, Pointe-Claire QC (CA)

( * ) Notice: Subject to any disclaimer, the term of this patent is extended or adjusted under 35 U.S.C. 154(b) by 17 days.

(21) Appl. No.: 15/057,642

(22) Filed: Mar. 1, 2016

(65) Prior Publication Data

US 2016/0257982 A1    Sep. 8, 2016

Related U.S. Application Data

(60) Provisional application No. 62/128,216, filed on Mar. 4, 2015.

(51) Int. Cl.

| | | |
|---|---|---|
| *C12P 19/14* | (2006.01) |
| *C12P 19/02* | (2006.01) |
| *C12P 7/56* | (2006.01) |
| *C12P 7/10* | (2006.01) |
| *C12P 7/16* | (2006.01) |
| *C12P 7/46* | (2006.01) |
| *D21C 9/16* | (2006.01) |
| *D21C 5/00* | (2006.01) |
| *D06L 4/15* | (2017.01) |

(52) U.S. Cl.
CPC .............. *C12P 19/14* (2013.01); *C12P 7/10* (2013.01); *C12P 7/16* (2013.01); *C12P 7/46* (2013.01); *C12P 7/56* (2013.01); *C12P 19/02* (2013.01); *D06L 4/15* (2017.01); *D21C 5/005* (2013.01); *D21C 9/166* (2013.01); *C12P 2201/00* (2013.01); *Y02E 50/10* (2013.01); *Y02E 50/16* (2013.01)

(58) Field of Classification Search
None
See application file for complete search history.

(56) References Cited

U.S. PATENT DOCUMENTS

2011/0177567 A1* 7/2011 Bakker ................. C12M 41/26
                                                            435/110
2013/0289268 A1* 10/2013 Teymouri ................. D21C 1/02
                                                            536/124

OTHER PUBLICATIONS

International Search Report of PCT/CA2016/050223.

* cited by examiner

*Primary Examiner* — Christian Fronda
(74) *Attorney, Agent, or Firm* — Norton Rose Fulbright Canada LLP

(57) ABSTRACT

The present disclosure relates to a process for extracting sugars from a pretreated lignocellulosic biomass. This process consists of contacting the pretreated lignocellulosic biomass with low charges of an aqueous peroxy acid (PA) solution to produce a liquid fraction (containing a small amount of lignin and hemicellulose degradation products) and a solid fraction containing cellulose, hemicellulose and lignin. The solid fraction can then be subjected to enzymatic hydrolysis with a variety of cell wall-degrading enzymes to produce a lignin-rich residue and a sugar solution that can be fermented to a variety of (bio)chemicals.

20 Claims, 7 Drawing Sheets

POST-TREATMENT TO ENHANCE THE ENZYMATIC HYDROLYSIS OF PRETREATED LIGNOCELLULOSIC BIOMASS

CROSS-REFERENCE TO RELATED APPLICATIONS

This application claims priority from U.S. provisional application Ser. No. 62/128,216 filed on Mar. 4, 2015. The content of the priority application is herewith incorporated in its entirety.

TECHNICAL FIELD

The present description relates to a process to increase the sugar yields during the enzymatic hydrolysis of pretreated lignocellulosic substrates.

BACKGROUND ART

Lignocellulosic biomass represents an abundant available raw material for the production of bio-fuels and bio-chemicals such as ethanol, butanol, lactic acid and succininc acid. It is composed of carbohydrate polymers (cellulose and hemicelluloses), and an aromatic polymer (lignin). The carbohydrate polymers contain different sugar monomers (six and five carbon sugars) and are tightly bound to lignin.

Lignocellulosic biomass is a potential source of sugars for the production of fuels and chemicals as it is relatively cheap and abundant. However, a significant challenge to the cost-competitive generation of sugars from biomass is the low accessibility of its polysaccharide components to hydrolytic enzymes and chemicals. This phenomenon is known as biomass recalcitrance and is largely governed by the presence and physicochemical properties of lignin in the plant cell wall. In addition to physically preventing the accessibility of cellulose and hemicelluloses to cell wall degrading enzymes (cellulases and hemicellulases), lignin contributes to biomass recalcitrance through hydrophobic interactions with the enzymes, decreasing their effective concentration. As a result, a pretreatment is required to reduce biomass recalcitrance.

However, because of the lack of selectivity of leading pretreatment technologies towards lignin, this type of fractionation/cell wall degradation is challenging. For example, while mild pretreatment conditions result in high carbohydrate recovery, the pretreated biomass retains the majority of its recalcitrance. On the other hand, more severe conditions typically generate substrates that are more amenable towards enzymatic saccharification. Unfortunately, this increase in susceptibility to enzymatic hydrolysis is accompanied by severe carbohydrate losses and the accumulation of carbohydrate-degradation products such as furfural and levulinic acid, which are inhibitory to downstream processes. As a result, pretreated biomass usually contains a substantial amount of residual lignin that remains associated with the carbohydrates (Chandra et al., 2007, Adv Biocehm Engin/Biotechnol, 108: 67-93).

Unfortunately, the residual lignin has a substantial effect on the enzymatic hydrolysis of pretreated lignocellulosic biomass. More specifically, lignin acts as both a physical barrier, which restricts the accessibility of carbohydrate-degrading enzymes to their substrates (Mooney et al., 1998, Biores. Technlo., 64: 113-119), and as an "attractant" to cellulases and hemicellulases, which decreases their effective concentration through non-productive binding (Yang and Wyman, 2006, Biotech. Bioeng., 94: 611-617). Consequently, relatively high enzyme loadings are required to achieve high carbohydrate conversion yields in a short time. Therefore, the need to decrease the enzyme loadings needed to achieve high carbohydrate 80%) conversion yields within a reasonable time period ($\leq 72$ h) is a challenge that needs to be addressed to improve the process economics.

There is thus still a need to be provided with a process for improving the conversion of lignocellulosic biomass to commercially useful products.

SUMMARY

In accordance with the present description there is now provided a process for improving the efficiency of the enzymatic hydrolysis of a pre-treated biomass comprising the steps of
a) treating the lignin-containing biomass with an aqueous solution of a peroxy acid (PA) increasing hydrophilicity of the lignin; and
b) hydrolyzing the lignin-containing biomass.

In accordance with an aspect of the process herein described, the treatment of the pretreated biomass with the aqueous solution of PA produces a liquid fraction and a solid fraction, said solid fraction containing cellulose and lignin with increased hydrophilicity and depending on the pretreatment process may contain hemicelluloses.

In accordance with another aspect of the process herein described, the hydrolysis of the solid fraction with a cellulase or other carbohydrate-degrading enzyme produces a sugar solution and a lignin-rich residue.

In accordance with yet another aspect of the process herein described, further comprising the step of isolating the sugar solution from the lignin-rich residue.

In accordance with still another aspect herein described, further comprising a first step of treating the pretreated biomass with a swelling agent prior to contacting said pretreated biomass with the PA solution.

In accordance with yet still another aspect of the process herein described, the swelling agent is an aqueous solution of sodium carbonate, an aqueous solution of potassium carbonate, an aqueous solution of sodium hydroxide, an aqueous solution of potassium hydroxide, concentrated phosphoric acid.

In accordance with a further aspect of the process herein described, the swelling agent is a polar organic solvent such as ethanol, methanol, butanol or N,N-dimethyl formamide.

In accordance with yet a further aspect of the process herein described, the pretreated lignocellulosic biomass is treated with the swelling agent at a temperature from 40° C. to about 150° C.

In accordance with still a further aspect of the process herein described, the solid fraction contains 90-95% of the total lignin present in the pretreated lignocellulosic biomass.

In accordance with yet still a further aspect of the process herein described, the PA solution contains at least one of performic acid, Caro's acid (peroxymonosulphuric acid) and peracetic acid (PAA).

In accordance with one embodiment of the process herein described, the PA content in the aqueous solution comprises 1.5 to 10% by weight of the pretreated biomass.

In accordance with another embodiment of the process herein described, the PA content in the aqueous solution comprises 1.5 to 4.5% by weight of the pretreated biomass.

In accordance with yet another embodiment of the process herein described, the PA content in the PA solution is 3% to 4.5% (w/w) of the pretreated biomass.

In accordance with still another embodiment of the process herein described, the PA solution further comprises at least one of acetic acid, hydrogen peroxide, sulphuric acid and water.

In accordance with yet still another embodiment of the process herein described, the ratio of pretreated biomass to PA solution is from 3:7 to 1:9.

In accordance with a further embodiment of the process herein described, the ratio of pretreated biomass to PA solution is from 3:7 to 1:6.

In accordance with yet a further embodiment of the process herein described, the pretreated biomass is contacted with the PA solution at a temperature between 45-85° C.

In accordance with yet still a further embodiment of the process herein described, the pretreated biomass is contacted with the PA solution at a temperature between 55 to 75° C.

In another aspect of the process herein described, the pretreated biomass is contacted with the PA solution at a temperature between 55 to 65° C.

In yet another aspect of the process herein described, the pretreated biomass is contacted with the PA solution at pressure of 1 to 10 atm.

In still another aspect of the process herein described, further comprising the step of separating the solid fraction from the liquid fraction prior to the hydrolysis step.

In yet still another aspect of the process herein described, the aqueous phase comprises at least one of formic acid, acetic acid, sulphuric acid, lignin-derived phenolic compounds and hemicellulose-derived sugars.

In a further aspect of the process herein described, further comprising the step of generating sodium acetate from the acetic acid in the aqueous phase and recycling said sodium acetate as a buffer for the hydrolysis of the solid fraction.

In yet a further aspect of the process herein described, the solid fraction is further washed with water at a temperature of 20° C. to about 90° C. to remove the phenolic compounds and hemicellulosic sugars prior to the hydrolysis step.

In still a further aspect of the process herein described, the solid fraction is further diluted to 10 to 20% w/w content prior to the hydrolysis step.

In accordance with another aspect of the process herein described, the pH of solid fraction is adjusted to a suitable pH.

In accordance with yet another aspect of the process herein described, the pH of the solid fraction is adjusted to a pH between 4.5 to 5.0.

In accordance with still another aspect of the process herein described, the pH of the solid fraction is adjusted with an aqueous buffer or with an aqueous alkaline solution.

In accordance with yet still another aspect of the process herein described, the aqueous buffer is a sodium acetate buffer or a sodium citrate buffer.

In accordance with a further aspect of the process herein described, the aqueous alkaline solution is a sodium carbonate solution, a potassium carbonate solution, a sodium hydroxide solution, a potassium hydroxide solution or an ammonia solution.

In accordance with yet a further aspect of the process herein described, the sugar solution is separated from the lignin-rich residue by centrifugation, pressing or filtration.

In accordance with still a further aspect of the process herein described, further comprising the step of fermenting the sugar solution with a suitable microorganism.

In accordance with yet still a further aspect of the process herein described, the sugar solution is converted by fermentation into ethanol, butanol, lactic acid or succinic acid.

In accordance with one embodiment of the process herein described, the sugar solution comprises C5 and C6 sugars.

In accordance with another embodiment of the process herein described, further comprising the step of treating the lignin-containing post-treated biomass with a cell-wall degrading enzyme concurrently with the hydrolysis of said lignin-containing post-treated biomass.

In accordance with yet another embodiment of the process herein described, the cell wall-degrading enzyme is at least one of a cellulase, a hemicellulase, a pectinase and a combination thereof.

In accordance with still another embodiment of the process herein described, the hemicellulase is a xylanase, a mannanase or a galactomannanase.

In accordance with yet still another embodiment of the process herein described, the pretreated biomass is derived from corn stover, a bioenergy crop, an agricultural residue, a wood chip, a sawdust, a forest residue, a wheat straw, grasses, a sludge, a byproduct from the paper manufacture or any combination thereof.

In accordance with further a embodiment of the process herein described, the pretreated biomass was pretreated by the TMP-Bio, organosolv, steam explosion, ammonia fiber explosion (AFEX), mechanical comminution, mechanical pulping, green liquor pretreatment, liquid hot water, SPORL, dilute acid hydrolysis process or a combination thereof.

In accordance with a yet further embodiment of the process herein described, the pretreated biomass comprises 10-60% w/w of lignin.

BRIEF DESCRIPTION OF THE DRAWINGS

Reference will now be made to the accompanying drawings.

DETAILED DESCRIPTION

It is provided a process for the conversion of lignocellulosic biomass such as wood chips, corn stover and other lignocellulosic materials to commercially useful products such as fermentable sugars. More specifically, it is provided a process to enhance the enzymatic saccharification of pretreated lignocellulosic materials.

Figure 1:
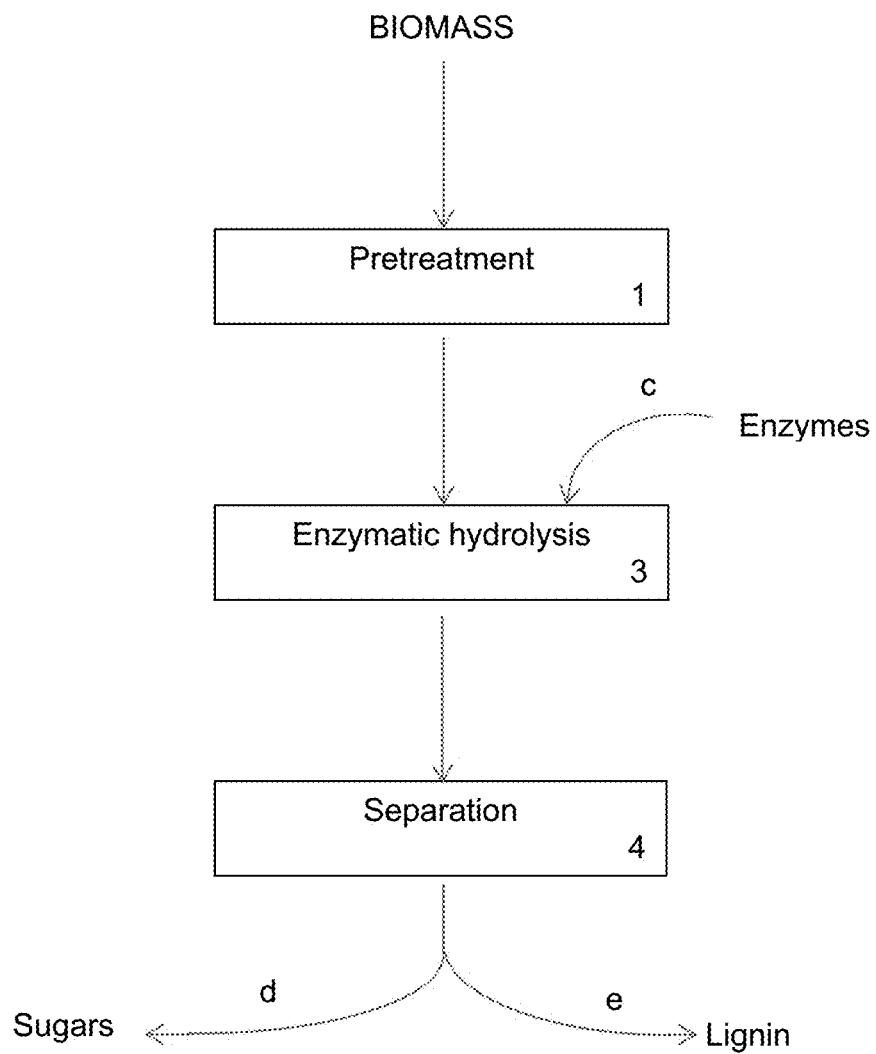
FIG. 1a illustrates schematically a process of extracting sugar as known in the art.
FIG. 1b illustrates schematically a process of extracting sugar according to an embodiment described herein.

As illustrated in FIG. 1a, known processes of extracting sugars from lignocellulosic biomass, such as described in WO 2011/057413, generally comprise a first step of pretreating the lignocellulosic biomass 1. After the pretreatment, cell wall-degrading enzymes c are added to enzymatically hydrolyse 3 the biomass in order to produce a lignin-rich residue e and a sugar solution d which can be separated 4 with known techniques.

Peroxy acids (PA's) such as performic acid, Caro's acid (peroxymonosulphuric acid) and peracetic acid (PAA) selectively oxidize the hydroxyl groups in lignin side chains to carbonyl groups and cleave β-aryl bonds, decreasing the molecular weight and increasing the hydrophilicity of lignin. In addition, PA's hydroxylate the aromatic moieties in lignin to form hydroquinones, which are further oxidized to water-soluble products such as muconic and maleic acid. These reactions lead to further lignin depolymerization and increase the hydrophilicity of the residual lignin in pretreated biomass.

Because of their high selectivity towards lignin, the roles of PAA and other PA's as delignifying/bleaching agents has been studied since 1948, particularly regarding their use to bleach chemical pulps. Moreover, PA's can be used as the main constituents of pulping liquor on a variety of lignocellulosic feedstocks to produce chemical pulps with low lignin contents (U.S. Pat. No. 4,793,898).

Within the context of a lignocellulosic biorefinery, the high (over 90%) delignification selectivity of PA's has led to their use as pretreatment agents to generate cellulose-rich substrates that are readily digested by cellulases (Teixeira et al., 2000, Appl. Biochem. Biotech., 84-86: 111-127; Zhao et al., 2007, J. Chem. Technol. Biotechnol., 82: 1115-1121; Zhao et al., 2008, Biores. Technol., 99: 3729-3736; and Zhao et al., 2009, Enzy. Microb. Technol., 44: 17-23). More recently, a two-stage organosolv process for the near-complete removal of lignin and hemicellulose from lignocellulosic biomass with solutions containing 5 to 95% (w/w of solution; however the actual charge on biomass was much higher depending on the liquid/biomass ratio) PAA has been proposed (U.S. patent application publication no. 2011/0151516). Briefly that process consists of treating the lignocellulosic material with an aqueous acetic acid solution which results in the near complete removal of the hemicellulosic sugars and partial delignification (Li et al., 2012, J. Agr. Food. Chem., 60: 1703-1712; Pan et al., 2006, Holzforschung., 60: 398-401). In the second step the partially delignified cellulose-enriched solid is treated with a peracetic acid solution for further delignification to produce a lignin-rich liquid fraction and a cellulose-rich solid that is readily digestible by cellulolytic enzymes. Essentially, lignin is completely removed and the cellulose is recovered before any hydrolysis step is conducted on the cellulose-rich fraction.

A major disadvantage of the known processes is that the effective delignification of lignocellulosic biomass (and subsequent improvements on the ease of cellulolytic hydrolysis) with PA's requires either very high chemical charges or a prior (partial) delignification step to reduce PA charges. For example at a biomass to solution ratio of 1:3, a 5% (w/w) solution of PA corresponds to a 15% charge by weight on the biomass. Moreover, while selective toward lignin, the conditions required to achieve effective delignification result in severe carbohydrate losses of 26 to 35% and thus require a pre-hydrolysis step to reduce those losses (Zhao et al., 2008, Biores. Technol., 99: 3729-3736; Zhao et al., 2009, Enzy. Microb. Technol., 44: 17-23; and U.S. patent application publication no. 2011/0151516). Finally, these processes generate a substantial amount of sugar and lignin-degradation products, which are known to inhibit fermentation processes (Jönsson et al., 2013, Biotechnol for Biofuels, 6: 16; Kim et al., 2013, Biores. Technol., 135: 30-38). Consequently, the separation (and washing) of the (cellulose-rich) solid from the liquid stream (containing the lignin and carbohydrate-degradation products) prior to enzymatic hydrolysis is often required to avoid detoxification of the hydrolysates.

Figure 1B:
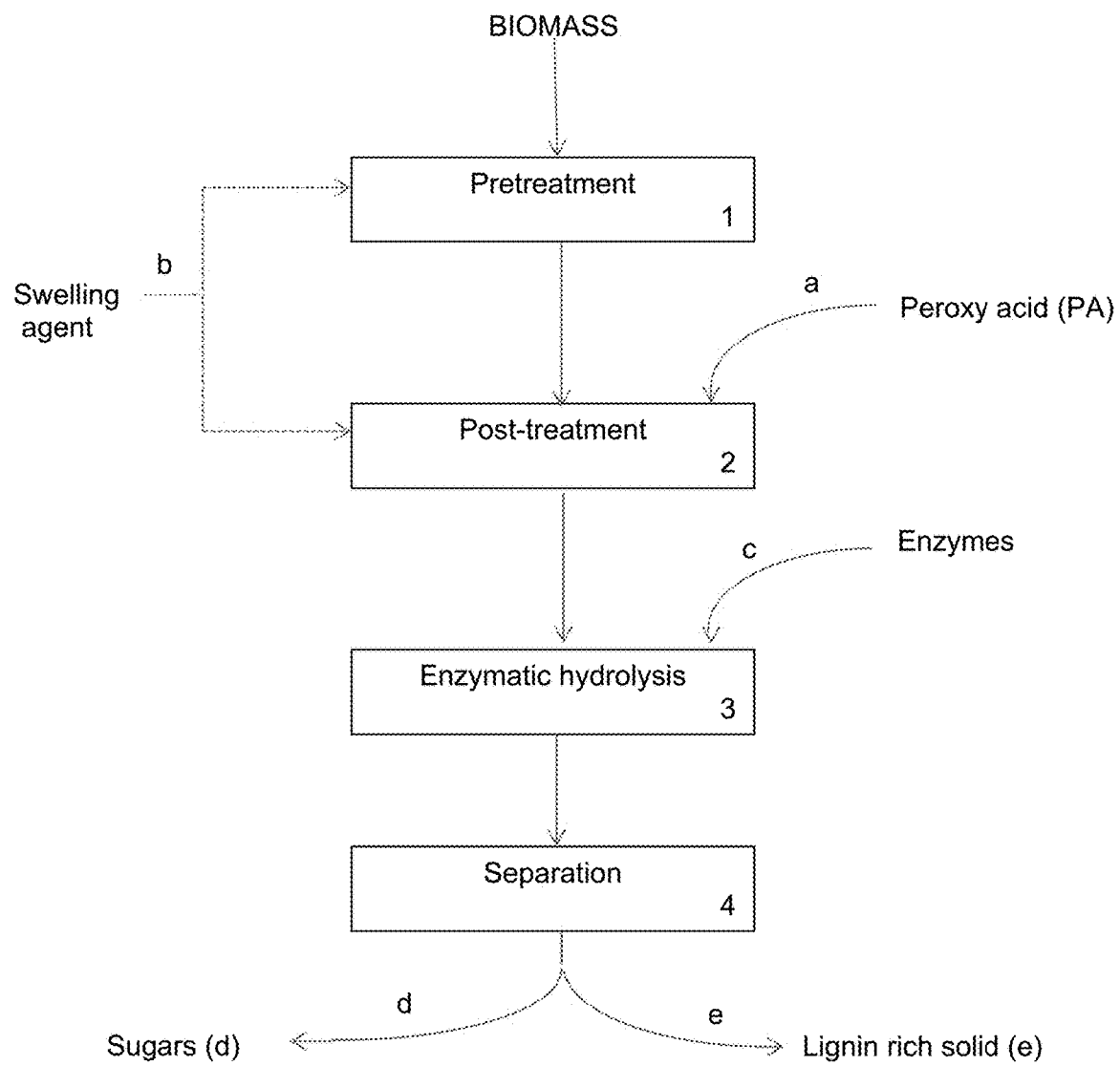

On the contrary, as described herein and as illustrated in FIG. 1b, it is disclosed a process provided which consists of contacting a pretreated lignocellulosic biomass 1 with low charges of an aqueous PA solution a (post-treatment 2) producing a liquid fraction (containing a small amount of lignin and hemicellulose degradation products) and a solid fraction containing cellulose, hemicellulose and lignin. The solid fraction can then be subjected to enzymatic hydrolysis 3 with a variety of cell wall-degrading enzymes c to produce a lignin-rich residue e and a sugar solution d after separation 4 that can be fermented to a variety of (bio)chemicals. It disclosed that although less than 4% of the starting material was removed (FIG. 2), the cellulose and hemicellulose conversion yields were substantially improved which was unexpected. It is further disclosed that the exposure of highly recalcitrant lignocellulosic biomass (such as mechanical pulp) to a swelling agent b prior to the post-treatment 2 with the PA solution a had a synergistic effect with regards to improving the efficiency of enzymatic hydrolysis. As indicated in FIG. 1b in dashed lines, step b is optional and dependent on the type of biomass. Briefly, the improvement in glucan and xylan conversion yields when the swelling agent and PA post-treatment were used sequentially were surprisingly much higher than the expected sum of the individual improvement in sugar conversion yield (for either glucan or xylan) from exposure to the swelling agent and PA post-treatment alone (Example V and Table 1). Furthermore, the high enzymatic hydrolysis and fermentation yields can be maintained without separating the solid and liquid fractions. Moreover when the peroxy acid employed is peracetic acid, the acetic acid generated as a byproduct can be utilized to produce sodium acetate buffer, which can be used to control reaction pH during enzymatic hydrolysis of the solid fraction. Finally, the process described herein can be readily integrated into biomass processing facilities such as pulp mills.

TABLE 1

Improvements in the enzymatic hydrolysis of hardwood mechanical pulp as the result of synergy between the swelling agent and the PA post-treatment

|  |  | 72 h conversion yield (%) | |
| --- | --- | --- | --- |
|  |  | Glucan | Xylan |
| A. | Without swelling agent and post-treatment | 23.3 | 22.3 |
| B. | With swelling agent | 30.1 | 36.2 |
| C. | With post-treatment | 35.6 | 39.6 |
| D. | Increase in yield by swelling agent (B − A) | 6.8 | 13.9 |
| E. | Increase in yield by post-treatment (C − A) | 12.3 | 17.3 |

TABLE 1-continued

Improvements in the enzymatic hydrolysis of hardwood mechanical pulp as the result of synergy between the swelling agent and the PA post-treatment

| | | 72 h conversion yield (%) | |
|---|---|---|---|
| | | Glucan | Xylan |
| F. | Expected increase in yield when both swelling agent and post- treatment are used in process (D + E) | 19.1 | 31.2 |
| G. | With swelling agent and post-treatment used sequentially in process | 84.9 | 92.9 |
| H. | Increase in yield when swelling agent and post-treatment used sequentially in process (G − A) | 61.6 | 70.6 |
| Synergy between swelling agent and post-treatment (H − F) | | 38.3 | 39.4 |

Advantageously, the post-treatment described herein retains over 96% of the starting material (including 90-95% of the initial lignin), the cellulose and hemicellulose components' susceptibility towards enzymatic hydrolysis at low enzyme loadings is surprisingly greatly enhanced. In addition, it is disclosed that the sugar and lignin-degradation products do not need to be removed from the post-treated material to achieve effective enzymatic hydrolysis and fermentation. Furthermore, exposure of highly recalcitrant lignocellulosic biomass (such as mechanical pulp) to a swelling agent followed by the post-treatment solution improves the enzymatic hydrolysis to a greater extent than the (expected) combined effect of the swelling agent and the post-treatment solution. Accordingly this observation is described as a synergistic effect between the swelling agent and this novel PA treatment. Overall, this novel post-treatment improves the efficiency of enzymatic hydrolysis and reduces the enzyme dosage or time required to obtain satisfactory carbohydrate conversion yields on a variety of lignocellulosic substrates including the (highly recalcitrant) high-lignin mechanical pulps.

Accordingly, in an embodiment, the process described herein allows enhancing the enzymatic hydrolysis of pretreated lignocellulosic biomass. In addition, the cost of enzymes used for such process is now greatly reduced as per the disclosure herewith. The process involves a post-treatment with peroxy acids (PA's) wherein the biomass containing lignin in the range of 10-60% w/w is treated with a solution comprising low (1.5 to 10% by weight on the biomass) charges of a PA under mild conditions (45-85° C. and atmospheric pressure) for a relatively short time (0.5 to 4 hours). This treatment is followed by an enzymatic hydrolysis step during which cellulases are added to convert cellulose to glucose. Optionally accessory cell-wall degrading enzymes such as hemicellulases and pectinases may also be added to hydrolyse hemicelluloses and pectin to other fermentable sugars such as xylose, mannose, and galactose and further enhance cellulose hydrolysis.

It is thus provided a process wherein the enzymatic hydrolysis of pretreated lignocellulosic biomass can be enhanced by subjecting it to a mild oxidative post-treatment with an aqueous solution containing a peroxy acid to yield a solid fraction that is highly susceptible to enzymatic hydrolysis. No matter whether there is a chemical treatment or not, the PA treatment is always the step just before the enzymatic hydrolysis.

As used herein, "lignocellulosic biomass" henceforth referred to as "biomass", refers to any material or mixture of materials derived from the plant cell wall and composed of cellulose, lignocellulose and lignin. Examples of biomass include but are not limited to: corn stover, bioenergy crops, agricultural residues, wood chips, sawdust, forest residues, wheat straw, grasses, sludge or byproducts from paper manufacture or any combination thereof.

As used herein, "pretreated biomass" refers to any biomass that has undergone a pretreatment to increase its accessibility to carbohydrate-degrading enzymes. Examples of pretreatments include but are not limited to: TMP-Bio, organosolv, steam explosion, ammonia fiber explosion (AFEX), mechanical comminution, mechanical pulping, green liquor pretreatment, liquid hot water (hydrothermolysis), the SPORL process, dilute acid hydrolysis and combinations thereof.

Figure 2:
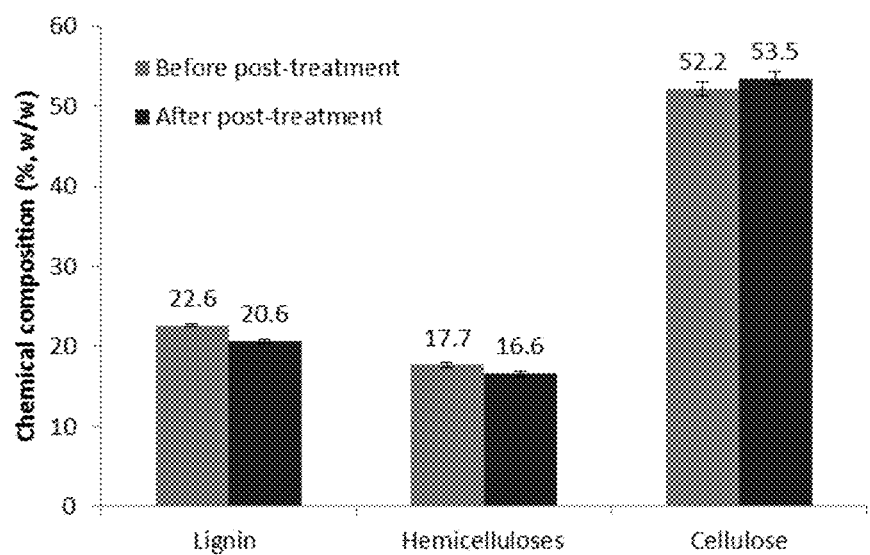
FIG. 2 shows the chemical composition of pretreated hardwood biomass before and after post-treatment at a peracetic acid charge of 4.5% (w/w on pretreated biomass).

Surprisingly, the mild conditions employed in the process described herein retain the majority of the lignin and hemicelluloses in the solid fraction (FIG. 2). The yield of the post-treated biomass was 96.4% and there are only marginal changes in lignin, cellulose and hemicellulose content (post-treatment conditions: 60° C., 70 minutes, 20 rpm, 20% solids (w/w); FIG. 2).

Figure 3:
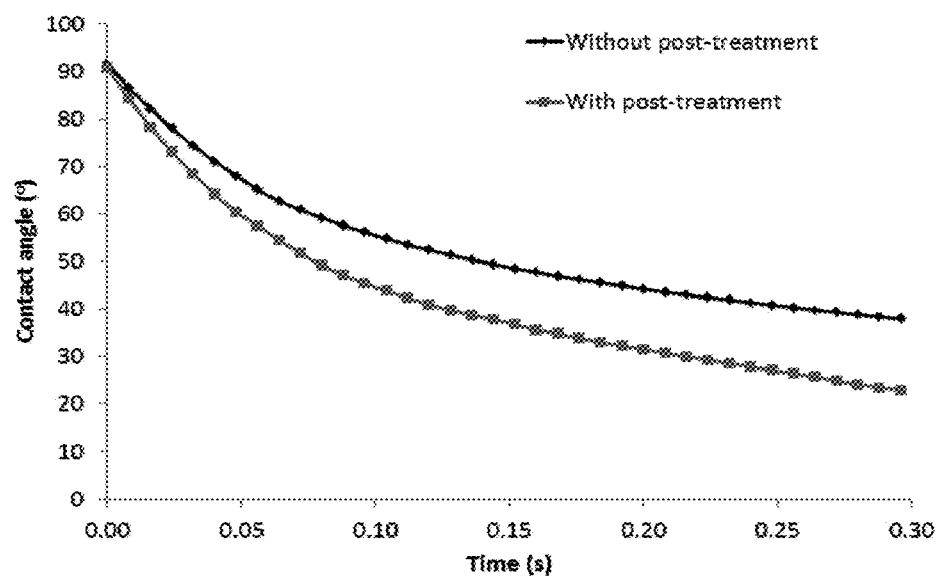
FIG. 3 shows the decrease in dynamic contact angle and therefore increase in hydrophilicity of pretreated hardwood biomass as a result of post-treatment at a peracetic acid charge of 4.5% (w/w on pretreated biomass).

While not wishing to be bound to theory, it is believed that the improvements in the susceptibility to enzymatic hydrolysis of the post-treated biomass are a direct result of the increased hydophilicity of the (partially oxidized) residual lignin (post-treatment conditions: 60° C., 70 minutes, 20 rpm, 20% solids (w/w); FIG. 3). Accordingly, the process described herein offers a novel way to improve the efficiency of enzymatic hydrolysis of lignocellulosic biomass with limited yield losses (≤4%). As a result, substantial reductions in the enzyme loadings or time required to achieve high carbohydrate conversion are achieved.

Depending on the nature of the pretreated biomass, it may be desirable to expose it to swelling agents to enhance peroxy acid uptake thereby reducing reaction time. Commonly employed swelling agents include but are not limited to: aqueous solutions of sodium carbonate, potassium carbonate, sodium hydroxide and potassium hydroxide, concentrated phosphoric acid and polar organic solvents such as ethanol, methanol, butanol and N,N-dimethyl formamide. Depending on the choice of swelling agent, these swelling treatments can be carried out at temperatures ranging from 40° C. to about 150° C.

Initially, the pretreated biomass is contacted with an aqueous solution containing a peroxy acid such as peracetic acid. Preferably, the amount of peroxy acid in the aqueous solution corresponds to a charge on the pretreated biomass of 1.5% to 10% w/w. More preferably, the peroxy acid content in the solution is 3% to 4.5% (w/w) on the pretreated biomass. Other constituents of the solution may comprise acetic acid, hydrogen peroxide, sulphuric acid and water. The ratio of pretreated biomass to solution is not particularly critical and may vary from about 3:7 to about 1:9 or lower. However to simplify downstream processing a pretreated biomass to solution ratio of about 3:7 to about 1:6 (corresponding to solid contents of 15-30% w/w) is most preferable.

The post-treatment is carried out at temperatures ranging from 45 to 85° C., preferably 55 to 75° C. more preferably 55 to 65° C. The post-treatment can be carried out at pressure range of 1 to 10 atm. However post-treatment at atmospheric pressure is most preferable.

Post-treatment time may also vary from 30 to 240 minutes, preferably from 60 to 120 minutes, more preferably from 60 to 90 minutes.

In an embodiment, the post-treated biomass may be optionally separated into a solid residue comprising the post-treated biomass and an aqueous phase containing acetic acid, a small amount of lignin-derived phenolic compounds and partially depolymerized hemicellulosic sugars in the form of xylo-oligomers. The solid residue may then be washed with water at a temperature of from about 20° C. to about 90° C. to completely remove the phenolic compounds and xylo-oligomers. The xylo-oligomers and phenolic compounds may be isolated from the aqueous phase(s) for further applications. The washed biomass may then be diluted to a suitable solid content (typically from 10 to 20% w/w), and subjected to enzymatic hydrolysis to obtain a sugar solution and a lignin-rich solid residue.

In a preferred embodiment, the post-treated biomass is not washed but rather the solid residue is either diluted or concentrated to a suitable solid content (from 10 to 30% w/w) followed by pH and temperatures adjustment and subjected to enzymatic hydrolysis to obtain a sugar solution and a lignin-rich residue.

Prior to enzymatic hydrolysis, the pH of the optionally washed post-treated biomass is adjusted to that at which cellulases and other cell wall-degrading enzymes display their optimum activity (typically between 4.5 and 5.0). The pH adjustment can be performed with an aqueous buffer (typically sodium acetate or sodium citrate) or with an aqueous alkaline solution. Examples of suitable alkaline solutions include but are not limited to sodium carbonate, sodium hydroxide, potassium hydroxide and ammonia. Another significant advantage of the process described herein is that when peracetic acid is used (and the post-treated biomass is not washed), the acetic acid generated as a byproduct of the reactions between peracetic acid and lignin can be directly used to generate the sodium acetate buffer used during the enzymatic hydrolysis step.

Enzymatic hydrolysis is performed with cellulases and optionally accessory cell wall-degrading enzymes such as hemicellulases (including xylanases mannanases and galactomannanases), pectinases and combinations thereof. Typically the cellulase dosage is in the range of 2.5 to 20 filter paper units (FPU) per gram of cellulose in the solid post-treated biomass.

In an embodiment, enzymatic hydrolysis is typically performed at a temperature range of 30 to 70° C. for a period of 24 to 120 hours.

After enzymatic hydrolysis, the sugars obtained may be separated from the lignin-rich solid using well-established techniques such as centrifugation, pressing and filtration.

The sugar solution may then be directly subjected to fermentation with a suitable microorganism to convert the sugars to a variety of (bio)chemicals. Examples of target (bio)chemicals include but are not limited to ethanol, butanol, lactic acid and succinic acid.

The sugar solution reflects the chemical composition of the pretreated biomass and is typically composed of C6 sugars or a mixture of C5 and C6, which may be co-fermented or purified and fermented separately.

As can be seen, the process described herein leads to significant improvements in cellulose and xylan hydrolysis yields. More specifically, as described in Example I, the post-treatment can substantially lower the enzyme charge required to achieve a target cellulose conversion yield at a specified time. For example, to obtain a 72 hour cellulose conversion yield of approximately 80 to 90%, the enzyme dosage can be reduced by half from 10 to 5 FPU $g^{-1}$ cellulose with the post-treatment.

On the other hand, as seen in Example II, the post-treatment described herein can also reduce the time required to achieve a target cellulose conversion yield at a fixed enzyme loading. More specifically, it shows that at an enzyme loading of 5 FPU $g^{-1}$ cellulose, post-treatment with a PAA charge of 4.5% (w/w on biomass) can reduce the time required for approximately 75% cellulose conversion from 72 hours to slightly over 24 hours.

The present disclosure will be more readily understood by referring to the following examples which are given to illustrate embodiments rather than to limit its scope.

Example I

Improvements in 72 h Enzymatic Hydrolysis Yields

A 30 g (oven dried weight equivalent) of never-dried pretreated hardwood biomass (generated as described in U.S. patent application no. 2011/0143411) was mixed for 3 minutes in a Hobart mixer with an aqueous solution containing peracetic acid at a charge of either 3% or 4.5% (w/w on biomass) and solid content of 20% (corresponding to a solid to liquid ratio of 1:4). The mixture containing the pretreated biomass and peracetic acid solution was then transferred to a 2000 ml laboratory peg mixer and heated at 60° C. for 70 minutes with mixing at 20 rpm. Following completion of the post-treatment, the biomass was cooled in an ice water bath, pressed and washed three times with 600 ml of distilled water at room temperature.

Figure 4A:
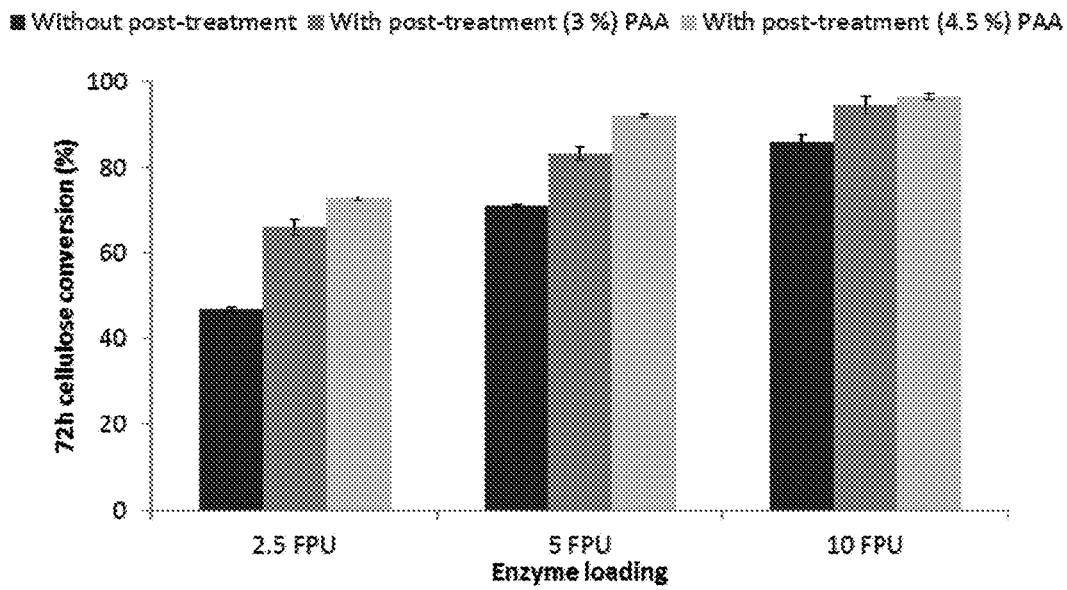
FIG. 4 shows the effect of post-treatment with peracetic acid at charges of 3 and 4.5% (w/w on pretreated biomass) on the 72 hour cellulose (a) and xylan (b) conversion yields at varying enzyme dosages (2.5 to 10 FPU $g^{-1}$ cellulose).
Figure 4B:
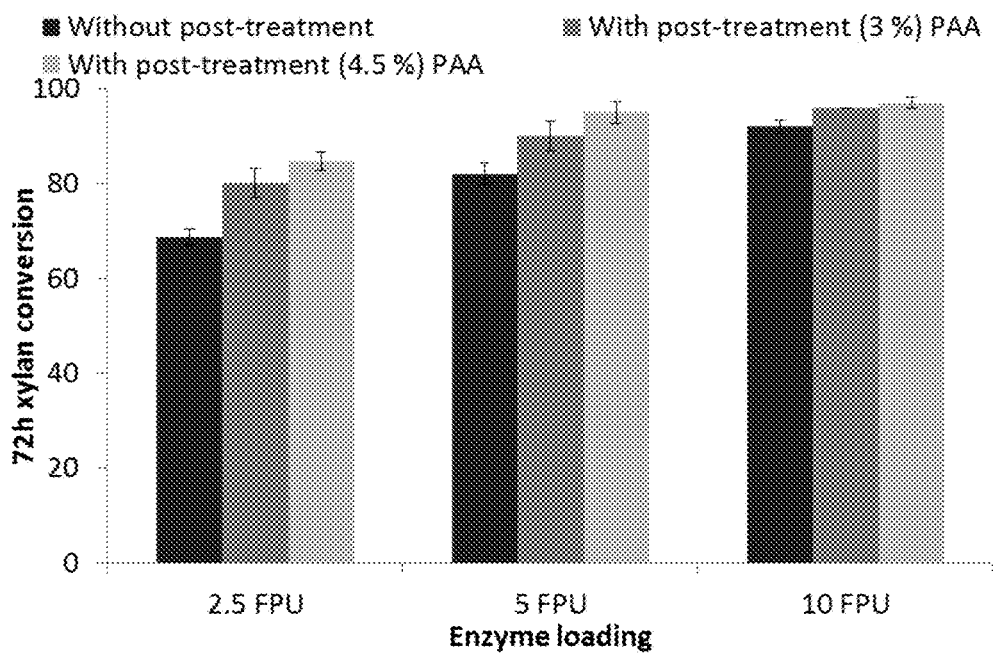

Batch hydrolysis of the biomass with and without post-treatment was performed at 10% (w/v) solids content in 50 mM acetate buffer, pH 4.8 with 0.004% tetracycline and 0.003% cycloheximide, to prevent microbial contamination. A Cellulase mixture containing β-glucosidase and hemicellulase activities (Ctec2, Novozymes, Franklinton N.C.) was used at loadings ranging from 2.5, to 10 FPU $g^{-1}$ of cellulose. The reaction mixture (50 mL) was incubated at 125 rpm, 50° C., in a rotary shaker and sampled for glucose and xylose a determination after 72 h by HPLC. All hydrolysis experiments were conducted in triplicate and the results are shown in FIG. 4.

Example II

Reduction in Time Required to Achieve a Target Cellulose Conversion Yield

Figure 5:
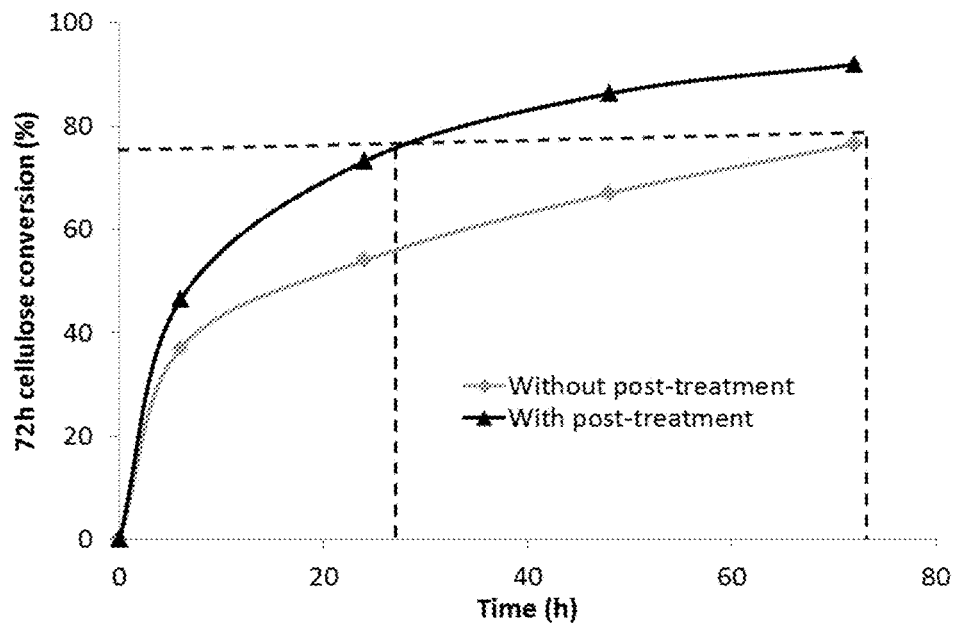
FIG. 5 illustrates the reduction in the time required to achieve a similar cellulose conversion yield as a result of post-treatment at a peracetic acid charge of 4.5% (w/w on pretreated biomass) while maintaining the enzyme loading constant.

The enzymatic hydrolysis experiments on pretreated hardwood biomass with and without post-treatment with a peracetic acid charge of 4.5% (w/w on biomass) were performed as described in Example I with the exceptions that a single enzyme loading of 5 FPU $g^{-1}$ cellulose was used and the reaction was also sampled after 24 and 48 hours to obtain a more complete cellulose hydrolysis profile. The results are shown in FIG. 5.

Example III

Post-Treatment can be Performed with or without a Washing Step

Figure 6:
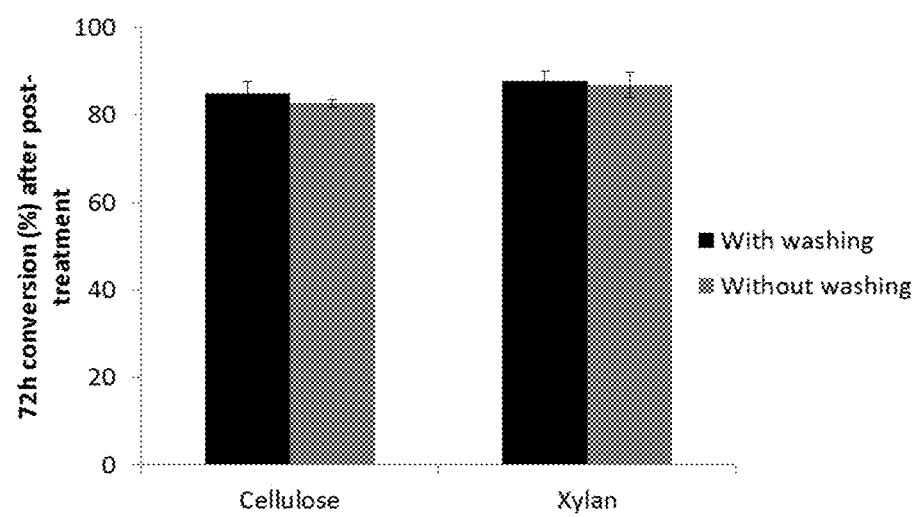
FIG. 6 shows the effect of washing on the 72 h cellulose and xylan conversion yields of the post-treated biomass.

Post-treatment at a peracetic acid charge of 3% (w/w on biomass) and enzymatic hydrolysis were performed as described in Example I with the exception that instead of being washed, the post-treated biomass was diluted to 10% solids and subjected to enzymatic hydrolysis at an enzyme loading of 10 FPU $g^{-1}$ cellulose. The results are shown in FIG. 6. Accordingly, similar cellulose and xylose conversion yields can be obtained with and without washing the solid substrate after the post-treatment.

Example IV

Post-Treatment does not Affect the Fermentability of the Post-Treated Biomass

Post-treatment at a peracetic acid charge of 3% (w/w on biomass) and enzymatic hydrolysis were performed as described in Example III. After 72 hours, the hydrolysates were incubated at 105° C. for 10 minutes to terminate the reaction followed by filtration in vacuo to separate the sugars from the lignin-rich solid. A control experiment was performed with biomass that was not subjected to the post-treatment. The sugar-rich filtrates were fermented to lactic acid as described by Bischoff et al. (2010, Biotechnol. Lett., 32: 823-828) with slight modifications. Briefly, the fermentation inoculum of *Bacillus coagulans* GBI 30, 6086 was produced by recovering cultures from a BSX agar plate (10 g $L^{-1}$ tryptone, 5 g $L^{-1}$ yeast extract, 2 g $L^{-1}$ $K_2HPO_4$, and 15 g $L^{-1}$ agar, after being grown from the stock culture at 50° C. static overnight) by inoculating 50 mL BSX media (10 g $L^{-1}$ tryptone, 5 g $L^{-1}$ yeast extract, 2 g $L^{-1}$ $K_2HPO_4$, and 10 g $L^{-1}$ xylose) with a colony and incubating at 50° C., static overnight.

Figure 7A:
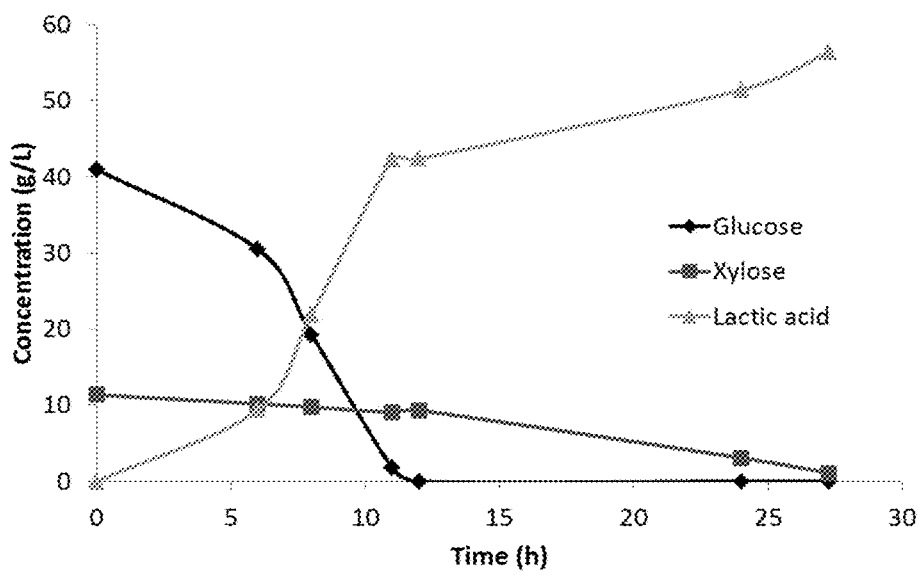
FIG. 7 compares the fermentability to lactic acid of sugar solutions obtained after enzymatic hydrolysis of pretreated hardwood biomass with (a) and without (b) post-treatment at a peracetic acid charge of 3% (w/w on pretreated biomass).
Figure 7B:
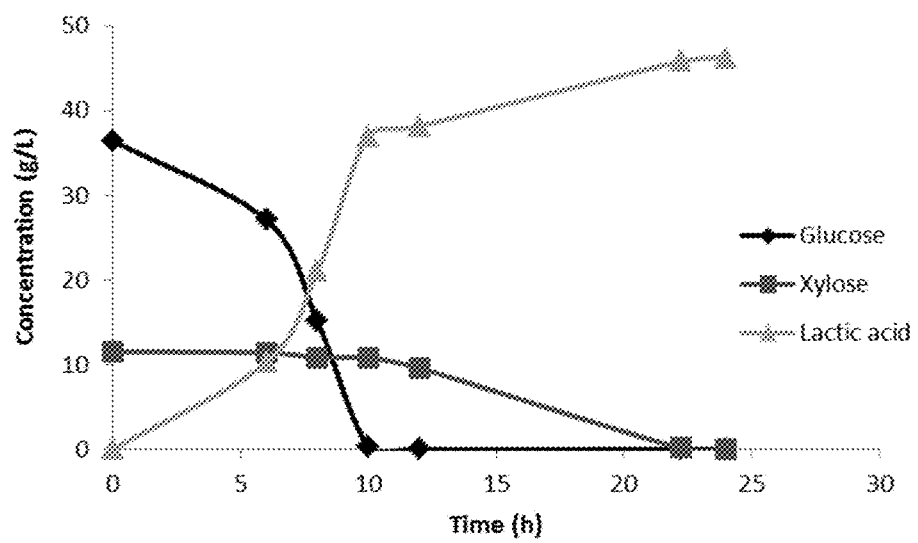

Fermentation was performed in a 1200 mL bio-reactor. Temperature was maintained at 50° C. with a water jacket and stirring was constant at 220 rpm. pH was kept between 6-6.5 by manual addition of 5 N NaOH. The process was anaerobic but not strictly, i.e. the bio-reactor was not purged with nitrogen before inoculation. Instead inoculation began in an aerobic environment, and the bacteria quickly consumed all the oxygen and the process became anaerobic. Growth media (tryptone, yeast extract, $K_2HPO_4$) were autoclaved at 121° C. for 20 min to sterilize prior to aseptic additions while the sugar solution was filtered through Nalgene™ Rapid-Flow™ Sterile disposable filter equipped with a 0.45 μm polyethersulfone (PES) membrane. 20 mL of (26.1 g $L^{-1}$ $K_2HPO_4$, 11.3 g $L^{-1}$ $KH_2PO_4$, and 25 g $L^{-1}$ $NH_4NO_3$) and 1 mL of (1.05 M nitrilotriacetic acid, 0.59 M $MgSO_4.7H_2O$, 0.91 M $CaCl_2.2H_2O$, and 0.04 M $FeSO_4.7H_2O$) were aseptically added per liter of the working volume. The inoculum represented 6-9% (v/v) of the working volume. Lactic acid yield at a certain time was calculated as grams of lactic acid produced per 100 g of fermented C5 and C6 sugars. The results are shown in FIG. 7. The biomass (i.e. sugar and lignin) degradation products generated during the post-treatment will not have a negative impact on the fermentability of the sugar-rich liquid fraction as the final lactic acid yield was 90%.

Example V

Figure 8:
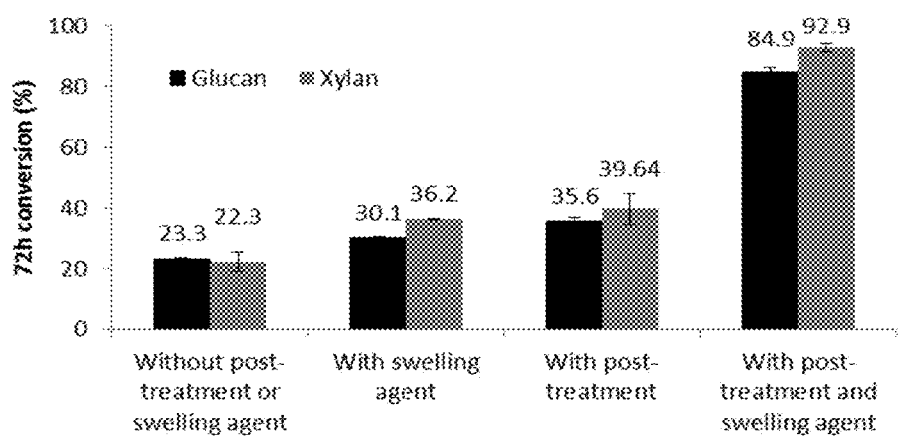
FIG. 8 shows the effect of post-treatment with peracetic acid at a charge of 4.5% (w/w on pretreated biomass) on the enzymatic hydrolysis of hardwood mechanical pulp with and without exposure to a swelling agent. Swelling conditions: 2.5% (w/w on biomass) NaOH, 80° C., 60 minutes.

Synergy Between a Swelling Agent and the PA Post-Treatment Improves the Enzymatic Hydrolysis Efficiency of Mechanical Pulps Post-treatment at a peracetic acid charge of 4.5% (w/w on biomass) and enzymatic hydrolysis (5 FPU $g^{-1}$ cellulose) were performed on hardwood mechanical pulp (a highly recalcitrant lignocellulosic substrate) as described in Example I with and without prior contact to a swelling agent. The results are shown in FIG. 8. Both post-treatment with PA's and treatment with swelling agent can enhance the enzymatic hydrolysis of highly-recalcitrant biomass. Surprisingly, when the biomass was treated sequentially with the swelling agent and PA's, there is a synergistic effect between the swelling agent and the post-treatment. More specifically, the improvement in sugar yield when swelling agent and post-treatment were used sequentially in the process was surprisingly much higher than the expected sum of the individual improvement in sugar conversion yield (for either glucan or xylan) from swelling agent and post-treatment alone (Table 1).

While the invention has been described in connection with specific embodiments thereof, it will be understood that it is capable of further modifications and this application is intended to cover any variations, uses, or adaptations of the invention following, including such departures from the present disclosure as come within known or customary practice within the art to which the invention pertains and as may be applied to the essential features hereinbefore set forth, and as follows in the scope of the appended claims.

What is claimed is:

1. A process for improving the efficiency of the enzymatic hydrolysis of a pre-treated biomass comprising the steps of
    a) treating the biomass containing lignin with a swelling agent and an aqueous solution of a peroxy acid (PA) increasing hydrophilicity of the lignin; and
    b) hydrolyzing the lignin-containing biomass.
2. The process of claim 1, wherein the treatment of the pretreated biomass with the aqueous solution of PA produces a liquid fraction and a solid fraction, said solid fraction containing cellulose and lignin with increased hydrophilicity and depending on the pretreatment process may contain hemicelluloses.
3. The process of claim 2, wherein the hydrolysis of the solid fraction with a cellulase or other carbohydrate-degrading enzyme produces a sugar solution and a lignin-rich residue.
4. The process of claim 3, further comprising the step of isolating the sugar solution from the lignin-rich residue.
5. The process of claim 1, further comprising a first step of treating the pretreated biomass with the swelling agent prior to contacting said pretreated biomass with the PA solution.
6. The process of claim 1, wherein the swelling agent is an aqueous solution of sodium carbonate, an aqueous solution of potassium carbonate, an aqueous solution of sodium hydroxide, an aqueous solution of potassium hydroxide, or concentrated phosphoric acid.
7. The process of claim 5, wherein the swelling agent is a polar organic solvent.
8. The process of claim 5, wherein the pretreated lignocellulosic biomass is treated with the swelling agent at a temperature from 40° C. to about 150° C.
9. The process of claim 3, wherein the solid fraction contains 90-95% of the total lignin present in the pretreated lignocellulosic biomass.
10. The process of claim 2, further comprising the step of separating the solid fraction from the liquid fraction prior to the hydrolysis step.
11. The process of claim 10, wherein the aqueous phase comprises at least one of formic acid, acetic acid, sulphuric acid, a lignin-derived phenolic compounds and hemicellulosic sugars.
12. The process of claim 11 further comprising the step of generating sodium acetate from the acetic acid in the aqueous phase and recycling said sodium acetate as a buffer for the hydrolysis of the solid fraction.
13. The process of claim 11, wherein the solid fraction is further washed with water at a temperature of 20° C. to about 90° C. to remove the phenolic compounds and hemicellulosic sugars prior to the hydrolysis step.

14. The process of claim 3, further comprising the step of fermenting the sugar solution with a suitable microorganism.

15. The process of any one of claim 1, further comprising the step of treating the lignin-containing post-treated biomass with a cell-wall degrading enzyme concurrently with the hydrolysis of said lignin-containing post-treated biomass.

16. The process of claim 15, wherein the cell wall-degrading enzyme is at least one of a cellulase, a hemicellulase, a pectinase and a combination thereof.

17. The process of claim 16, wherein the hemicellulase is a xylanase, a mannanase or a galactomannanase.

18. The process of claim 1, wherein the pretreated biomass is derived from corn stover, a bioenergy crop, an agricultural residue, a wood chip, a sawdust, a forest residue, a wheat straw, grasses, a sludge, a byproduct from the paper manufacture or any combination thereof.

19. The process of claim 1, wherein the pretreated biomass was pretreated by the TMP-Bio, organosolv, steam explosion, ammonia fiber explosion (AFEX), mechanical comminution, mechanical pulping, green liquor pretreatment, liquid hot water, SPORL, dilute acid hydrolysis process or a combination thereof.

20. The process of claim 1, wherein the pretreated biomass comprises 10-60% w/w of lignin.

* * * * *